United States Patent [19]

Eri et al.

[11] Patent Number: 4,801,573

[45] Date of Patent: Jan. 31, 1989

[54] CATALYST FOR PRODUCTION OF HYDROCARBONS

[75] Inventors: Sigrid Eri, Trondheim, Norway; James G. Goodwin, Jr.; George Marcelin, both of Pittsburgh, Pa.; Trygve Riis, Oslo, Norway

[73] Assignee: 501 Den Norske Stats Oljeslenskap A.S., Trondheim, Norway

[21] Appl. No.: 113,095

[22] Filed: Oct. 23, 1987

[51] Int. Cl.[4] .................... B01J 21/04; B01J 23/68
[52] U.S. Cl. ........................ 502/302; 502/303; 502/304; 502/324; 502/328; 502/332; 518/715
[58] Field of Search ............... 502/332, 302, 303, 304, 502/324, 328; 518/715

[56] References Cited

U.S. PATENT DOCUMENTS

| 3,389,965 | 6/1968 | Ruiter et al. | 502/332 X |
| 4,568,663 | 2/1986 | Mauldin | 518/715 X |
| 4,613,624 | 9/1986 | Beuther et al. | 518/715 |

FOREIGN PATENT DOCUMENTS

| 48-66086 | 9/1973 | Japan | 502/332 |
| 468649 | 4/1975 | U.S.S.R. | 502/332 |
| 610558 | 6/1978 | U.S.S.R. | 502/332 |

*Primary Examiner*—W. J. Shine
*Attorney, Agent, or Firm*—Kirkpatrick & Lockhart

[57] ABSTRACT

A catalyst for converting synthesis gas composed of hydrogen and carbon monoxide to hydrocarbons. The catalyst includes cobalt in catalytically active amounts up to about 60 wt % of the catalyst and rhenium in catalytically active amounts of about 0.5 to 50 wt % of the cobalt content of the catalyst supported on alumina. A metal oxide promoter may be added.

13 Claims, 2 Drawing Sheets

Fig. 1.

Effect of Rhenium on CO Conversion
Catalysts Containing 12% Cobalt

Fig. 2.

Effect on Conversion of Adding Rhenium to Cobalt on Alumina Catalyst.

4,801,573

CATALYST FOR PRODUCTION OF HYDROCARBONS

BACKGROUND OF THE INVENTION

1. Field of the Invention

The present invention relates to catalysts and more particularly to a catalyst for converting synthesis gas to hydrocarbons.

2. Description of the Prior Art

The reaction to convert carbon monoxide and hydrogen mixtures (defined herein as synthesis gas or syngas) to higher hydrocarbons over metallic catalysts has been known since the turn of the century. This reaction is commonly referred to as the Fischer-Tropsch or F-T synthesis. The F-T synthesis was exploited commercially during World War II in Germany. By 1944 a total of nine F-T plants were operating in Germany, primarily using a catalyst composed of cobalt, magnesium oxide, thorium oxide and kieselguhr, in the relative proportions of 100:5:8:200. Later, most of the thoria was replaced by magnesia, primarily for economic reasons. Currently, commercial Fischer-Tropsch plants are operating in South Africa. These plants use a precipitated iron-based catalyst which contains various promoters to improve the stability and product distribution.

The common F-T catalysts are nickel, cobalt and iron. Nickel was probably the first substance to be recognized as capable of catalyzing the reaction of syngas to hydrocarbons, producing mainly methane (see, for example, "The Fischer-Tropsch Synthesis" by R. B. Anderson, Academic Press (1984), p.2). Iron and cobalt are able to produce longer chain length hydrocarbons and are thus preferred as catalysts for the production of liquid hydrocarbons. However, other metals are also capable of catalyzing the F-T synthesis. Ruthenium is a very active catalyst for the formation of hydrocarbons from syngas. Its activity at low temperatures is higher than that of iron, cobalt or nickel; and it produces a high proportion of heavy hydrocarbons. At high pressures, it produces a high proportion of high molecular weight wax. Osmium has been found to be moderately active, while platinum, palladium and iridium exhibit low activities (see Pichler, "Advances in Catalysis", vol. IV, Academic Press, N.Y., 1952). Other metals which are active, such as rhodium, yield high percentages of oxygenated materials (Ichikawa, Chemtech, 6, 74 (1982)). Other metals that have been investigated include rhenium, molybdenum and chromium, but these exhibit very low activities with most of the product being methane.

Various combinations of metals can also be used for synthesis. Doping cobalt catalysts with nickel causes an increase in methane production during F-T synthesis (see "Catalysis", vol. IV, Reinhold Publishing Co., (1956), p.29). In U.S. Pat. No. 4,088,671 to T. P. Kobylinski, entitled "Conversion of Synthesis Gas Using a Cobalt-Ruthenium Catalyst", the addition of small amounts of ruthenium to cobalt is shown to result in an active F-T synthesis catalyst with a low selectivity to methane. Thus, these references teach that the combination of two or more metals can result in an active F-T catalyst. In general, the catalysts of these teachings have activities and selectivities which are within the ranges of the individual components.

Combinations of metals with certain oxide supports have also been reported to result in an improved hydrocarbon yield during F-T synthesis, probably due to an increase in the surface area of the active metal. The use of titania to support cobalt or cobalt-thoria is taught in U.S. Pat. No. 4,595,703, entitled "Hydrocarbons from Synthesis Gas". In this case the support serves to increase the activity of the metal(s) toward hydrocarbon formation. In fact, titania belongs to a class of metal oxides known to exhibit strong metal-support interactions and, as such, has been reported to give improved F-T activity for a number of metals (see, for example, S. J. Tauster et al, Science, 211, 1121 (1981)). Combinations of titania and two or more metals have also been shown to yield improved F-T activity. In U.S. Pat. No. 4,568,663, entitled "Cobalt Catalysts In the Conversion of Methanol to Hydrocarbons and for Fischer-Tropsch Synthesis", combinations of cobalt, rhenium and thoria and cobalt and rhenium supported on titania are claimed useful for the production of hydrocarbons from methanol or synthesis gas. This patent also indicates that similar improvements in activity can be obtained when cobalt-rhenium or cobalt-rhenium-thoria is compounded with other inorganic oxides. However, titania is the only support specifically discussed. The typical improvement in activity gained by promotion of cobalt metal supported on titania with rhenium is less than a factor of 2. We have found that the addition of rhenium to cobalt metal supported on a number of other common supports results in similar improvements in activity.

The only other examples in the literature of catalysts involving mixtures of cobalt and rhenium refer to completely different chemical reactions. For example, in Soviet Union Pat. No. 610558, a catalyst composed of cobalt and rhenium supported on alumina is taught to result in improved performance for the steam reforming of hydrocarbons. Steam reforming of hydrocarbons is a process completely different from hydrocarbon production via F-T synthesis and is believed to proceed by a completely different mechanism. Although some steam reforming catalysts can convert synthesis gas to hydrocarbons, such catalysts are not selective for the production of high carbon-number hydrocarbons (C3 and above) during conversion of synthesis gas. In fact, most commonly used steam reforming catalysts contain nickel as their active metal, and nickel produces mostly methane when used for syngas conversion.

SUMMARY OF THE INVENTION

It has been found in accordance with the present invention that synthesis gas comprising hydrogen and carbon monoxide can be converted to liquid hydrocarbons by using a catalyst consisting of cobalt and rhenium supported on alumina. The catalyst preferably contains from about 5 to 60% cobalt and has a rhenium content between 0.5 and 50% of the amount of cobalt. The alumina preferably is gamma alumina.

It has been found that the addition of small amounts of rhenium to catalysts consisting predominantly of cobalt supported on alumina unexpectedly results in greatly enhanced activity of this catalyst for hydrocarbon production from syngas. This is surprising in light of the fact that rhenium supported on alumina shows very low activity, with most of the product being methane. Furthermore, rhenium addition to cobalt supported on supports other than alumina results in catalysts with much lower activity levels. In addition, the more active cobalt plus rhenium catalyst maintains the high selectivity to higher hydrocarbons and the low selectivity to methane found with an alumina-supported cobalt catalyst. Both the high activity and the low methane production of cobalt-rhenium on alumina are unexpected in light of the facts that (1) rhenium shows very low activity for F-T synthesis, (2) the main products from F-T synthesis over a rhenium catalyst are methane and carbon dioxide, and (3) the use of alumina as a support for catalysts containing only cobalt results in no, or at best only a slight, increase in activity compared to the use of cobalt on other supports. Thus, for reasons not fully understood, the combination of cobalt and rhenium supported on alumina results in a catalyst which is significantly more active than either of the two individual metals supported on alumina or the combination of the two metals supported on other inorganic supports, such as silica, magnesia, silica-alumina, titania, chromia or zirconia. Furthermore, the product distribution with a high selectivity to $C_2+$ hydrocarbons and low selectivity to methane and carbon dioxide would not have been predicted based on the known product distribution from rhenium catalysts.

DETAILED DESCRIPTION OF THE PREFERRED EMBODIMENTS

The catalyst of the present invention comprises as the active catalytic ingredients cobalt and rhenium supported on alumina with rhenium present in a relatively smaller amount than cobalt. This catalyst has been found to be highly active for the conversion of synthesis gas, a mixture of hydrogen and carbon monoxide, into a mixture of predominantly paraffinic hydrocarbons. As indicated above, it has long been known that cobalt is an active catalyst for the F-T synthesis. It is also known that the addition of rhenium to a cobalt catalyst supported on titania gives improved activity, even if rhenium by itself shows very low activity for F-T synthesis and produces methane as the main product. Surprisingly, we have found that the choice of support for the cobalt plus rhenium catalyst is very critical, and that the addition of rhenium to an alumina-supported cobalt catalyst gives a much higher improvement in activity than addition of rhenium to cobalt supported on other inorganic oxides.

The cobalt is added to the alumina support in some amount up to about 60 wt % of the catalyst, including cobalt. Preferably, amounts between 5 and 45 wt % are used; and more preferably between 10 and 40 wt %. The content of rhenium is between about 0.5 and 50 wt % of the cobalt content; preferably between 1 and 30 wt %; and more preferably from about 2 to around 20 wt %.

In addition to cobalt and rhenium, it is beneficial to include a small amount of a metal oxide promoter in an amount between about 0.1 and 5 wt %, and more preferably between about 0.2 and 2 wt %, based on the weight of the complete catalyst. The promoter is suitably chosen from elements in groups IIIB, IVB and VB of the periodic chart, the lanthanides and actinides. The promoter oxide can be chosen from, for example, $Sc_2O_3$, $Y_2O_3$, $La_2O_3$, $Ce_2O_3$, $Pr_2O_3$, $ZrO_2$, $Ac_2O_3$, $PaO_2$, $Nd_2O_3$, $CeO_2$, $V_2O$ or $Nb_2O_5$. The most preferable oxide is $La_2O_3$, or a mixture of lanthanides, rich in lanthanum. Oxides like MnO or MgO can also be included. While not essential, the use of these metal oxides is common in the art, since they are believed to promote the production of products with higher boiling points, while maintaining or improving catalytic activity. However, the catalyst is highly active and selective without the addition of a promoter.

The Catalyst Support

The catalytically active metals and the promoter metal oxide, if present, are distended on alumina. Although other supports may be used, it has been found, for example, that silica, titania, chromia, magnesia, silica-alumina and zirconia produce catalysts with much lower activities.

To be most effective when used as a support, alumina should be characterized by low acidity, high surface area, and high purity. These properties are necessary in order to enable the catalyst to have high activity and a low deactivation rate, and to produce high molecular weight hydrocarbon products. The surface area of the alumina support is at least, and preferably greater than, about 100 m$^2$/g; and more preferably at least about 150 m$^2$/g. The pore volume is at least, and preferably greater than, about than 0.3 cm$^3$/g. The catalyst support must be of high purity. That is, the content of elements, e.g. sulfur and phosphorous, that have a deleterious effect on catalytic activity must be kept low. The sulfur content of the catalyst support should be kept below 100 ppm and preferably below 50 ppm. Although gamma alumina has generally been used and is preferred, a number of alumina structures, if prepared properly, can meet these conditions and are suitable supports. For example, eta-aluminna, xi-alumina, theta-alumina, delta-alumina, kappa-alumina, boehmite and pseudo-boehmite can all be used as supports.

Catalyst Preparation

The method of depositing the active metals and the promoter oxide on the alumina support is not critical, and can be chosen from various methods well known to those skilled in the art. One suitable method that has been employed is known as incipient wetness impregnation. In this method the metal salts are dissolved in an amount of a suitable solvent just sufficient to fill the pores of the catalyst. In another method, the metal oxides or hydroxides are coprecipitated from an aqueous solution by adding a precipitating agent. In still another method, the metal salts are mixed with the wet support in a suitable blender to obtain a substantially homogeneous mixture. In the present invention, if incipient wetness impregnation is used, the catalytically active metals can be deposited on the support using an aqueous or an organic solution. Suitable organic solvents include, for example, acetone, methanol, ethanol, dimethyl formamide, diethyl ether, cyclohexane, xylene and tetrahydrofuran. Aqueous impregnation is preferred when $Co(NO_3)_2$ is used as the salt, while an organic solvent is the preferred solvent when the catalyst is prepared from cobalt carbonyl.

Suitable cobalt compounds include, for example, cobalt nitrate, cobalt acetate, cobalt chloride and cobalt carbonyl, with the nitrate being the most preferable when impregnating from an aqueous solution. Suitable rhenium compounds include, for example, rhenium oxide, rhenium chloride and perrhenic acid. Perrhenic acid is the preferred compound when preparing a catalyst using an aqueous solution. The promoter can suitably be incorporated into the catalyst in the form, for example, of the nitrate or chloride.

After aqueous impregnation, the catalyst is dried at 110° to 120° C. for 3 to 6 hours. When impregnating from organic solvents, the catalyst is preferably first dried in a rotary evaporator apparatus at 50° to 60° C. under low pressure, then dried at 110° to 120° C. for several hours longer.

The dried catalyst is calcined under flowing air by slowly increasing the temperature to an upper limit of between 200 and 500° C., preferably between 250° and 350° C. The rate of temperature increase is preferably between 0.5° and 2° C. per minute, and the catalyst is held at the highest temperature for a period of 2 to 5 hours. The impregnation procedure is repeated as many times as necessary to obtain a catalyst with the desired metals content. Cobalt, rhenium and the promoter, if present, can be impregnated together, or in separate steps. If separate steps are used, the order of impregnating the active components can be varied.

Before use, the calcined catalyst is preferably reduced with hydrogen. This can suitably be done in flowing hydrogen at atmospheric pressure at a flow rate between 30 and 100 cm³/min when reducing about 2 g of catalyst. The flow rate should suitably be increased for larger quantities of catalyst. The temperature is increased at a rate between 0.5° and 2° C. per minute from ambient to a maximum level of 250° to 450° C., preferably between 300° and 400° C., and maintained at the maximum temperature for about 6 to 24 hours, more preferably 10 to 24 hours.

After the reduction step, the catalysts may be oxidized and rereduced before use. To carry out the oxidation step, the catalyst is treated with dilute oxygen (1-3% oxygen in nitrogen) at room temperature for a period of ½ to 2 hours before the temperature is increased at the same rate and to the same temperature as used during calcination. After holding the high temperature for 1 to 2 hours, air is slowly introduced, and the treatment is continued under air at the high temperature for another 2 to 4 hours. The second reduction is carried out under the same conditions as the first reduction.

Hydrocarbon Synthesis

The reactor used for the synthesis of hydrocarbons from synthesis gas can be chosen from various types well known to those skilled in the art, for example, fixed bed, fluidized bed, ebullating bed or slurry. The catalyst particle size for the fixed or ebullating bed is preferably between 0.1 and 10 mm and more preferably between 0.5 and 5 mm. For the other types of operations a particle size between 0.01 and 0.2 mm is preferred.

The synthesis gas is a mixture of carbon monoxide and hydrogen and can be obtained from any source known to those skilled in the art, such as, for example, steam reforming of natural gas or partial oxidation of coal. The molar ratio of $H_2:CO$ is preferably between 1:1 to 3:1; and more preferably between 1.5:1 to 2.5:1. Carbon dioxide is not a desired feed component for use with the catalyst of this invention, but it does not adversely affect the activity of the catalyst. All sulfur compounds must, on the other hand, be held to very low levels in the feed, preferably below 1 ppm.

The reaction temperature is suitably between 150° and 300° C.; and more preferably between 175° and 250° C. The total pressure can be from atmospheric to around 100 atmospheres, preferably between 1 and 30 atmospheres. The gaseous hourly space velocity, based on the total amount of synthesis gas feed, is preferably between 100 and 20,000 cm³ of gas per gram of catalyst per hour; and more preferably from 1000 to 10,000 cm³/g/h, where gaseous hourly space velocity is defined as the volume of gas (measured at standard temperature and pressure) fed per unit weight of catalyst per hour.

The reaction products are a complicated mixture, but the main reaction can be illustrated by the following equation:

$$nCO + 2nH_2 \rightarrow (-CH_2-)_n + nH_2O$$

where $(-CH_2-)_n$ represents a straight chain hydrocarbon of carbon number n. Carbon number refers to the number of carbon atoms making up the main skeleton of the molecule. In F-T synthesis, the products are generally either paraffins, olefins, or alcohols. Products range in carbon number from one to 50 or higher.

In addition, with many catalysts, for example those based on iron, the water gas shift reaction is a well known side reaction:

$$CO + H_2O \rightarrow H_2 + CO_2$$

With cobalt catalysts the rate of this last reaction is usually very low. However, it is found that, even though rhenium catalysts exhibit a relatively high selectivity to carbon dioxide, the cobalt plus rhenium catalyst of this invention surprisingly does not have a higher selectivity to carbon dioxide than the cobalt only catalyst.

The hydrocarbon products from Fischer-Tropsch synthesis are distributed from methane to high boiling compounds according to the so called Schulz-Flory distribution, well known to those skilled in the art. The Schulz-Flory distribution is expressed mathematically by the Schulz-Flory equation:

$$W_i = (1-\alpha)^2 i \alpha^{i-1}$$

where i represents carbon number, $\alpha$ is the Schulz-Flory distribution factor which represents the ratio of the rate of chain propagation to the rate of chain propagation plus the rate of chain termination, and $W_i$ represents the weight fraction of product of carbon number i.

The products produced by the catalyst of this invention generally follow the Schulz-Flory distribution, except that the yield of methane is usually higher than expected from this distribution. This indicates that methane is apparently produced by an additional mechanism.

It is well known, and also shown in one of the following examples, that rhenium alone is a low activity catalyst for Fischer-Tropsch synthesis producing a product which is predominantly methane. On the other hand, cobalt is a well known catalyst for producing higher carbon number hydrocarbons. In U.S. Pat. No. 4,568,663, it has been shown that adding small amounts of rhenium to cobalt supported on titania improves the catalytic activity. In the present invention, it has been found that the hydrocarbon yield obtained by adding rhenium is surprisingly much larger for an alumina supported cobalt catalyst than that obtained from cobalt and rhenium on several other inorganic supports. The improved activity is followed by no deleterious effect on the selectivity to methane.

The catalyst of this invention is further described in the following examples.

Experimental Work

The following examples describe the preparation of various catalysts and the results obtained from testing these catalysts for conversion of synthesis gas into hydrocarbons.

Before being tested, each catalyst was given a pretreatment consisting of reduction by passing hydrogen over the catalyst at a rate of 3000 cm$^3$/g/h while heating the catalyst at a rate of 1° C./min to 350° C. and maintaining this temperature for 10 hours. In the tests, synthesis gas consisting of 33 vol % carbon monoxide and 67 vol % hydrogen was passed over 0.5 g of the catalyst at atmospheric pressure at temperatures of 185°, 195° and 205° C. according to the following schedule:

9 hr. 50 min. at 195° C.
4 hr. 20 min. at 205° C.
4 hr. 30 min. at 185° C.
9 hr. 50 min. at 195° C.

The flow rate of synthesis gas was 1680 cm$^3$/g of catalyst/h. Products from the reactor were sent to a gas chromatograph for analysis. Catalysts were compared based on the results over the period from 10 to 30 hours on stream.

EXAMPLE 1

Catalyst Containing Cobalt But No Rhenium

This example describes the preparation of a control cobalt catalyst which was used for comparative purposes. This catalyst was prepared as follows:

A solution was prepared by dissolving 17.03 g of cobalt nitrate, $Co(NO_3)_2.6H_2O$, and 0.76 g of mixed rare earth nitrate, $RE(NO_3)_3$, where RE stands for rare earth with a composition of 66% $La_2O_3$, 24% $Nd_2O_3$, 8.2% $Pr_6O_{11}$, 0.7% $CeO_2$, and 1.1% other oxides (Molycorp 5247), in 30 ml of distilled water. The total solution was added with stirring to 25 g of Ketjen CK300 gamma-alumina which had been calcined 10 hours at 500° C. The prepared catalyst was then dried for 5 hours in an oven at a temperature of 115° C. The dried catalyst was then calcined in air by raising its temperature at a heating rate of 1° C./minute to 300° C. and holding at this temperature for 2 hours. The finished catalyst contained 12 wt % cobalt and 1 wt % rare earth oxide with the remainder being alumina. This catalyst is referred to as preparation "a" in Table I. The above procedure was repeated to produce preparation "b" catalyst in Table I.

The results of the tests with this catalyst are shown in Table I. In this and the following tables, selectivity is defined as the percent of the carbon monoxide converted that goes to the indicated product.

TABLE I

| Temp. °C. | Preparation | CO Conversion % | $C_2+$ Selectivity % | $CH_4$ Selectivity % | $CO_2$ Selectivity % |
|---|---|---|---|---|---|
| 185 | a | 7 | 91.1 | 7.2 | 1.7 |
|  | b | 11 | 91.8 | 7.1 | 1.1 |
| 195 | a | 12 | 90.0 | 8.9 | 1.1 |
|  | b | 18 | 90.2 | 9.0 | 0.8 |
| 205 | a | 21 | 87.7 | 11.3 | 1.0 |
|  | b | 29 | 86.7 | 12.4 | 0.9 |

This example shows that a cobalt catalyst exhibits good selectivity to ethane and longer chain length hydrocarbons and low selectivity to methane and carbon dioxide.

EXAMPLE 2

Catalyst Containing Rhenium But No Cobalt

This example describes a rhenium catalyst prepared for comparative purposes. The procedure employed was the same as for Example 1 except that the solution contained 0.33 g of perrhenic acid, $HReO_4$ as 82.5% aqueous solution, and 0.54 g of rare earth nitrate to make 24 ml of solution which then was added to 20 g of calcined alumina. The finished catalyst contained 1 wt % rhenium and 1 wt % rare earth oxide with the remainder being alumina.

The results of the tests with the catalyst of Example 2 are shown in Table II.

TABLE II

| Temp. °C. | CO conversion % | $C_2+$ Selectivity % | $CH_4$ Selectivity % | $CO_2$ Selectivity % |
|---|---|---|---|---|
| 185 | 0.3 | 20 | 30 | 50 |
| 195 | 0.3 | 19 | 31 | 50 |
| 205 | 0.3 | 19 | 31 | 50 |

EXAMPLE 3

Catalyst Containing Rhenium But No Cobalt

Repetition of the procedure from Example 2, except that 0.83 g of perrhenic acid were used, gave a catalyst containing 4 wt % rhenium. The results of the tests with the catalyst of Example 3 are shown in Table III.

TABLE III

| Temp. °C. | CO conversion % | $C_2+$ Selectivity % | $CH_4$ Selectivity % | $CO_2$ Selectivity % |
|---|---|---|---|---|
| 185 | 0.3 | 20 | 30 | 50 |
| 195 | 0.3 | 19 | 31 | 50 |
| 205 | 0.3 | 19 | 31 | 50 |

The results from Examples 2 and 3 show that catalysts containing rhenium but no cobalt have very low activity for producing desirable liquid hydrocarbons from synthesis gas. Furthermore, about half the product is carbon dioxide, and most of the hydrocarbon product is methane.

EXAMPLES 4 THROUGH 11

Catalysts Containing Both Cobalt And Rhenium

The preparation procedure of Example 1 was employed except that varying amounts of perrhenic acid were added to the solution. This produced a series of catalysts containing 12 wt % cobalt and 0.1, 0.2, 0.3, 0.5, 1.0, 2.0, 4.0, and 8.0 wt % rhenium in addition to 1.0 wt % rare earth oxide.

Figure 1:
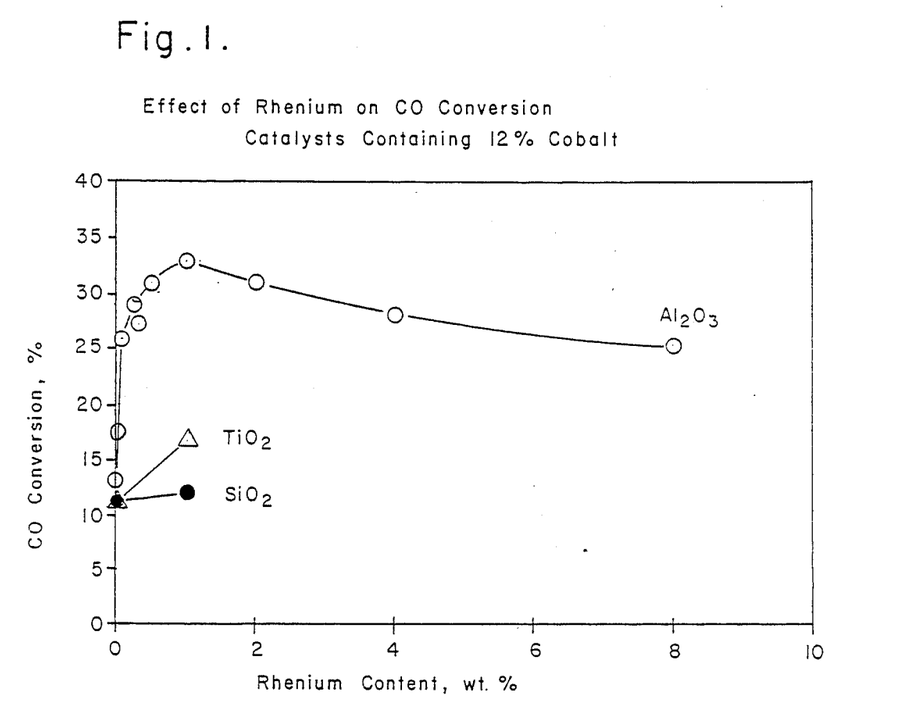
FIG. 1 is a graph showing the effect of rhenium content on CO conversion using catalysts containing 12% cobalt.

The results of the tests with the catalysts of Examples 4 through 11 at 195° C. are shown in Table IV and further illustrated in FIG. 1. FIG. 1 shows the effect on carbon monoxide conversion of adding rhenium to catalysts containing 12% cobalt.

TABLE IV

| Example No. | Co wt % | Re wt % | CO conversion % | C₂+ Selectivity % | CH₄ Selectivity % | CO₂ Selectivity % |
|---|---|---|---|---|---|---|
| 4 | 12 | 0.1 | 26 | 89.8 | 9.6 | 0.6 |
| 5 | 12 | 0.2 | 29 | 88.9 | 10.4 | 0.7 |
| 6 | 12 | 0.3 | 27 | 88.2 | 11.0 | 0.8 |
| 7 | 12 | 0.5 | 31 | 88.3 | 10.9 | 0.8 |
| 8 | 12 | 1.0 | 33 | 87.7 | 11.4 | 0.9 |
| 9 | 12 | 2.0 | 31 | 85.7 | 13.3 | 1.0 |
| 10 | 12 | 4.0 | 28 | 84.7 | 14.2 | 1.1 |
| 11 | 12 | 8.0 | 25 | 84.5 | 14.2 | 1.3 |

As can be seen from comparison of the results in Table I with Table IV and FIG. 1, the addition of small amounts of rhenium to a cobalt supported on alumina catalyst significantly increases the conversion of the carbon monoxide in the feed. Levels of rhenium as low as 0.1 wt % result in approximately doubling the CO conversion. The exact level of Re for optimum activity is very important, as the rate of carbon monoxide conversion increases rapidly at low rhenium addition levels, reaches a maximum and then decreases gradually at levels greater than 1 wt % rhenium. However, even at the highest rhenium level investigated (8%), a clear improvement in conversion is evident when compared to the catalyst not containing rhenium.

It is important that the increase in activity occur without a corresponding increase in either the methane or the carbon dioxide selectivities. Table IV shows that the increase in carbon monoxide conversion is not accompanied by any substantial change in either the selectivities to methane or carbon dioxide. Thus, after rhenium addition the principal reaction products are still desirable hydrocarbons.

EXAMPLES 12 THROUGH 25

Catalysts Containing Both Cobalt and Rhenium

The preparation procedure of Example 1 was employed except that varying amounts of cobalt nitrate and perrhenic acid were added to the solution. This produced a series of catalysts containing from 3.0 to 40 wt % cobalt and from 0 to 5.0 wt % rhenium in addition to 1.0 wt % rare earth oxide.

The results of the tests with the catalysts of Examples 12 through 25 at 195° C. are shown in Table V.

TABLE V

| Example No. | Co wt % | Re wt % | CO Conversion % | C₂+ Selectivity % | CH₄ Selectivity % | CO₂ Selectivity % |
|---|---|---|---|---|---|---|
| 12 | 3 | 0.0 | 5 | 90.7 | 8.1 | 1.2 |
| 13 | 3 | 0.25 | 4 | 87.2 | 10.4 | 2.4 |
| 14 | 6 | 0.0 | 12 | 90.0 | 8.9 | 1.1 |
| 15 | 6 | 0.5 | 16 | 88.2 | 10.8 | 1.0 |
| 16 | 9 | 0.0 | 15 | 90.0 | 9.1 | 0.9 |
| 17 | 9 | 0.75 | 25 | 88.1 | 11.1 | 0.8 |
| 18 | 20 | 0.0 | 20 | 89.3 | 9.8 | 0.9 |
| 19 | 20 | 0.5 | 40 | 87.9 | 11.1 | 1.0 |
| 20 | 20 | 1.0 | 46 | 86.1 | 12.9 | 1.0 |
| 21 | 20 | 5.0 | 42 | 83.9 | 14.8 | 1.3 |
| 22 | 40 | 0.0 | 20 | 89.3 | 9.7 | 1.0 |
| 23 | 40 | 1.0 | 56 | 85.0 | 13.2 | 1.8 |
| 24 | 40 | 2.0 | 58 | 84.3 | 13.7 | 2.0 |
| 25 | 40 | 5.0 | 60 | 81.9 | 15.7 | 2.4 |

Figure 2:
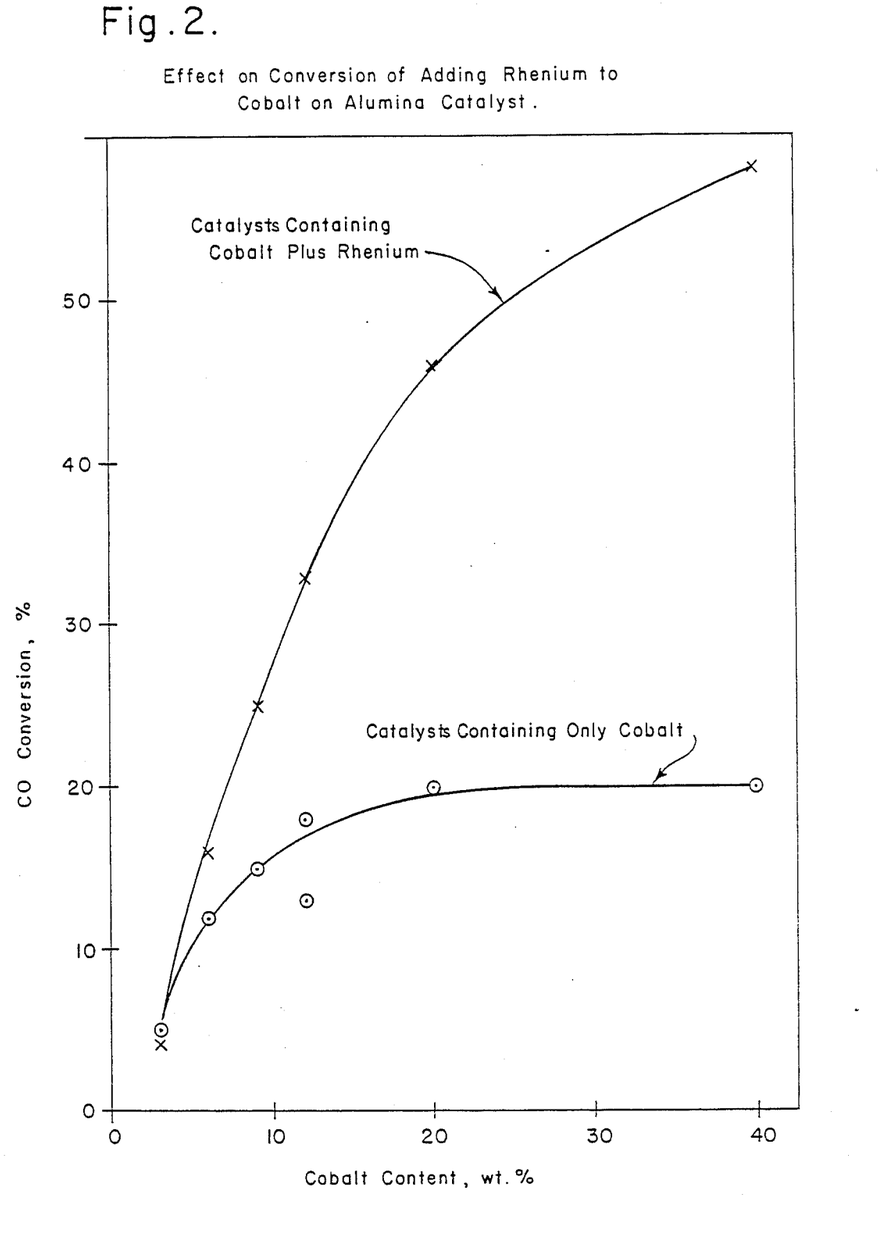
FIG. 2 is a graph showing the effect on CO conversion of adding rhenium to catalysts containing various amounts of cobalt on an alumina support.

The results in Table V show that for cobalt catalysts without rhenium, there is a significant increase in activity in going from 3% cobalt to 6% cobalt. However, only modest increases in activity occur from this point up to cobalt loadings of as high as 40%. At a cobalt loading of 3%, the addition of rhenium does not improve the catalytic activity, but the improvement upon rhenium addition is significant for higher cobalt loadings. In fact, the improvement in activity due to the addition of rhenium increases as the cobalt content increases as shown in FIG. 2.

EXAMPLES 26 AND 27

Cobalt/Rhenium Catalysts with Promoters

To illustrate the use of promoters other than rare earth oxides, the following catalysts were prepared. The preparation procedure used to prepare the catalyst of Example 8 was used except that zirconium nitrate, $Zr(NO_3)_4$, or vanadyl oxalate, $VO(C_2O_4H)_3$, was substituted for the rare earth nitrate. The results of tests at 195° C. with the catalysts of examples 26 and 27 are shown in Table VI. In addition to the promoter, these catalysts contained 12% cobalt and 1% rhenium and were supported on alumina.

TABLE VI

| Example No. | Promoter | CO conversion % | C₂+ Selectivity % | CH₄ Selectivity % | CO₂ Selectivity % |
|---|---|---|---|---|---|
| 26 | ZrO₂ (0.75 wt %) | 31 | 87.9 | 11.3 | 0.8 |
| 27 | V₂O₅ (0.56 wt %) | 26 | 89.4 | 9.8 | 0.8 |

EXAMPLES 28 THROUGH 41

Cobalt/Rhenium Catalysts On Other Supports

For comparison with alumina, several catalysts were prepared on other supports. The preparation procedure used to prepare the catalyst of Example 8 was repeated, but without the addition of rare earth oxide. The titanium-supported catalysts were prepared on titania calcined at both 500° C. and 600° C. After calcination at 600° C., the titania is mainly in the crystalline rutile form; while after calcination at 500° C. the anatase:rutile ratio is about 1:1. The catalysts prepared on the titania support calcined at these two temperatures showed exactly the same catalytic activity.

The supports used were: Davison Grade 59 silica; Degussa P25 titania; Alpha Chemicals No. 88272 chromia; magnesia prepared by calcining Fischer basic magnesium carbonate; American Cyanamid AAA Silica-Alumina; and Alpha Chemicals 11852 zirconia (containing 2% alumina). Information on the composition of the catalysts prepared on the different supports is given in Table VII.

TABLE VII

| Example No. | Support | Weight of Support g | Weight of Materials in Impregnating Solution, g | | Composition of Finished Catalyst, wt % | |
|---|---|---|---|---|---|---|
| | | | Co(NO₃)₂ | HReO₄* | Co | Re |
| 28 | Silica | 20 | 13.47 | — | 12 | — |
| 29 | Silica | 20 | 13.62 | 0.38 | 12 | 1.0 |
| 30 | Titania** | 25 | 16.84 | — | 12 | — |
| 31 | Titania** | 24.64 | 16.78 | 0.46 | 12 | 1.0 |
| 32 | Titania*** | 25 | 16.84 | — | 12 | — |
| 33 | Titania*** | 24.64 | 16.78 | 0.46 | 12 | 1.0 |
| 34 | Chromia | 20 | 13.47 | — | 12 | — |
| 35 | Chromia | 21.3 | 14.51 | 0.40 | 12 | 1.0 |
| 36 | Magnesia | 21.59 | 14.54 | — | 12 | — |
| 37 | Magnesia | 14.54 | 10.67 | 0.29 | 12 | 1.0 |
| 38 | Silica-Alumina | 20 | 13.47 | — | 12 | — |
| 39 | Silica-Alumina | 20 | 13.62 | 0.38 | 12 | 1.0 |
| 40 | Zirconia | 20 | 13.47 | — | 12 | — |
| 41 | Zirconia | 20 | 13.62 | 0.38 | 12 | 1.0 |

*Weight of 82.5% perrhenic acid solution.
**Calcined at 500° C.
***Calcined at 600° C.

A series of tests was conducted to evaluate the activities of the catalysts of the above examples in converting synthesis gas into hydrocarbons. The results of the tests with the catalysts of Examples 28 through 41 at 195° C. are shown in Table VIII. The results from catalysts prepared on alumina are included for comparison.

TABLE VIII

| Example No. | Co % | Re % | Support | CO Conversion % | $C_2+$ Selectivity % | $CH_4$ Selectivity % | $CO_2$ Selectivity % |
|---|---|---|---|---|---|---|---|
| 1 | 12 | — | $Al_2O_3$ | 12 | 90.0 | 8.9 | 1.1 |
| 8 | 12 | 1 | $Al_2O_3$ | 33 | 87.7 | 11.4 | 0.9 |
| 28 | 12 | — | $SiO_2$ | 11 | 90.1 | 8.7 | 1.2 |
| 29 | 12 | 1 | $SiO_2$ | 12 | 88.1 | 10.7 | 1.2 |
| 30 | 12 | — | $TiO_2$* | 11 | 87.6 | 11.8 | 0.6 |
| 31 | 12 | 1 | $TiO_2$* | 17 | 86.5 | 12.8 | 0.7 |
| 32 | 12 | — | $TiO_2$** | 11 | 87.6 | 11.7 | 0.7 |
| 33 | 12 | 1 | $TiO_2$** | 17 | 85.8 | 13.5 | 0.7 |
| 34 | 12 | — | $Cr_2O_3$ | 1 | 83.5 | 15.5 | 1.0 |
| 35 | 12 | 1 | $Cr_2O_3$ | 2 | 80.8 | 12.3 | 6.9 |
| 36 | 12 | — | MgO | 0.3 | 20.0 | 30.0 | 50.0 |
| 37 | 12 | 1 | MgO | 0.3 | 19.1 | 30.9 | 50.0 |
| 38 | 12 | — | $SiO_2/Al_2O_3$ | 5 | 76.3 | 22.2 | 1.5 |
| 39 | 12 | 1 | $SiO_2/Al_2O_3$ | 6 | 78.6 | 19.8 | 1.6 |
| 40 | 12 | — | $ZrO_2$ | 4 | 80.9 | 16.3 | 2.8 |
| 41 | 12 | 1 | $ZrO_2$ | 7 | 78.8 | 18.7 | 2.5 |

*Support calcined at 500° C.
**Support calcined at 600° C.

The catalysts in Table VII were prepared to test the teaching that various inorganic supports are acceptable for preparing cobalt plus rhenium F-T catalysts. An examination of the data in Table VIII leads to the surprising conclusion that the type of support is extremely important and that vast differences in activity exist between catalysts prepared on one support and catalysts of the same catalytic metals content on another support. More surprisingly, only cobalt plus rhenium on alumina showed a commercially attractive activity level and selectivity.

Catalysts on magnesia and chromia exhibited extremely low activities, both with and without rhenium. Catalysts on zirconia and silica-alumina showed somewhat higher activities, but selectivity to $C_2+$ hydrocarbons was poor. These catalysts showed only modest improvements in activity upon the addition of rhenium.

Catalysts without rhenium supported on silica and titania showed activity levels close to comparable cobalt on alumina catalyst. However, upon addition of rhenium, the alumina catalyst showed a surprising increase in activity from about 15% carbon monoxide conversion to 33% carbon monoxide conversion; whereas, the silica supported catalyst showed only a very small increase in activity from 11% carbon monoxide conversion to 12% carbon monoxide conversion, while the titania supported catalyst showed a larger, but still modest, gain in activity from 11% carbon monoxide conversion to 17% carbon monoxide conversion.

From these examples, plus those presented previously, it can be concluded that the catalytic activity of a cobalt catalyst supported on alumina is greatly improved by adding minor amounts of rhenium, as long as the cobalt level is greater than about 5 wt %. Although improved activity from rhenium addition is also observed for some other supports, the activity level achieved by adding rhenium to a catalyst supported on alumina is much higher than for other supports. This result is surprising and would not have been predicted based on teachings in the prior art.

What is claimed is:

1. A catalyst for converting synthesis gas to hydrocarbons comprising amounts of cobalt catalytically active in a Fischer-Tropsch synthesis and relatively lesser amounts of rhenium than the cobalt content composited on an alumina support.

2. The catalyst recited in claim 1 wherein cobalt is present in amounts ranging from 5 to about 60 wt % of the catalyst.

3. The catalyst recited in claim 1 wherein cobalt is present in amounts ranging from about 10 to about 40 wt % of the catalyst.

4. The catalyst recited in claim 1 wherein rhenium is present in amounts ranging from about 0.5 to 50 wt % of the cobalt content of the catalyst.

5. The catalyst recited in claim 1 wherein rhenium is present in amounts ranging from about 1 to 30 wt % of the cobalt content of the catalyst.

6. The catalyst recited in claim 1 wherein said support is gamma alumina.

7. The catalyst recited in claim 1 wherein said support has a surface area of at least about 100 m²/g and a pore volume of at least about 0.3 cm³/g.

8. The catalyst recited in claim 1 further comprising an effective amount of a promoter selected from the group consisting of oxides of the elements chosen from grous III B, IV B and V B of the periodic table, the lanthanides and the actinides, MgO and MnO, and mixtures thereof.

9. The catalyst recited in claim 8 wherein said promoter is present in an amount ranging from about 0.1 to 5 wt % of the catalyst.

10. A catalyst for converting synthesis gas to hydrocarbons comprising cobalt and rhenium composited on an alumina support wherein cobalt is present in catalytically active amounts up to about 60 wt % of the catalyst and rhenium is present in catalytically active amounts from about 0.5 to about 50 wt % of the cobalt content of the catalyst.

11. The catalyst recited in claim 10 further comprising an effective amount of a promoter selected from the group consisting of oxides of the elements chosen from the groups III B, IV B and V B of the periodic table, the lanthanides and the actinides, MgO and MnO, and mixtures thereof.

12. The catalyst recited in claim 10 wherein said support has a surface area of at least about 150 $m^2/g$ and a pore volume of at least about 0.3 $cm^3/g$.

13. The catalyst recited in claim 10 wherein the sulfur content of the alumina support is kept to levels below about one hundred parts per million.

UNITED STATES PATENT AND TRADEMARK OFFICE
CERTIFICATE OF CORRECTION

PATENT NO. : 4,801,573
DATED : January 31, 1989
INVENTOR(S) : Sigrid Eri et al.

It is certified that error appears in the above-identified patent and that said Letters Patent is hereby corrected as shown below:

Title page:

In the Assignee: Delete "501 Den Norske Stats Oljeslenskap A.S., Trondheim, Norway" and substitute therefor --Den Norske Stats Oljeselskap A.S., Trondheim, Norway--.

Col. 2, line 10, delete "et al," and substitute therefor --et al.--.

Col. 4, line 36, delete "eta-aluminna" and substitute therefor --eta-alumina--.

Col. 13, line 4, delete "grous" and substitute therefor --groups--.

Signed and Sealed this

Twenty-sixth Day of December, 1989

Attest:

JEFFREY M. SAMUELS

*Attesting Officer*         *Acting Commissioner of Patents and Trademarks*